United States Patent
Hiromoto et al.

(10) Patent No.: US 9,155,816 B2
(45) Date of Patent: Oct. 13, 2015

(54) MAGNESIUM-BASED MEDICAL DEVICE AND MANUFACTURING METHOD THEREOF

(71) Applicant: NATIONAL INSTITUTE FOR MATERIALS SCIENCE, Ibaraki (JP)

(72) Inventors: Sachiko Hiromoto, Ibaraki (JP); Akiko Yamamoto, Ibaraki (JP); Norio Maruyama, Ibaraki (JP); Toshiji Mukai, Ibaraki (JP); Hidetoshi Somekawa, Ibaraki (JP)

(73) Assignee: NATIONAL INSTITUTE FOR MATERIALS SCIENCE, Ibaraki (JP)

(*) Notice: Subject to any disclaimer, the term of this patent is extended or adjusted under 35 U.S.C. 154(b) by 121 days.

(21) Appl. No.: 13/709,519

(22) Filed: Dec. 10, 2012

(65) Prior Publication Data
US 2013/0129908 A1    May 23, 2013

Related U.S. Application Data

(62) Division of application No. 12/515,089, filed as application No. PCT/JP2007/072316 on Nov. 16, 2007, now abandoned.

(30) Foreign Application Priority Data

Nov. 17, 2006    (JP) .................................. 2006-311596

(51) Int. Cl.
*A61L 27/00* (2006.01)
*A61L 27/04* (2006.01)
(Continued)

(52) U.S. Cl.
CPC ............... *A61L 27/00* (2013.01); *A61L 27/047* (2013.01); *A61L 27/32* (2013.01); *A61L 27/58* (2013.01); *C23C 22/22* (2013.01)

(58) Field of Classification Search
CPC ........... A61B 2017/00836; A61B 2017/00831; A61L 27/00
USPC .......................................................... 606/298
See application file for complete search history.

(56) References Cited

U.S. PATENT DOCUMENTS 3,687,135 A * 8/1972 Stroganov et al. ............... 606/76
4,955,886 A * 9/1990 Pawluk ......................... 606/280
(Continued)

FOREIGN PATENT DOCUMENTS

JP    4-224747      8/1992
JP    2000-93503    4/2000
(Continued)

OTHER PUBLICATIONS

International Search Report mailed Dec. 25, 2007 for International Application No. PCT/JP2007/072316.
(Continued)

*Primary Examiner* — Christian Sevilla
(74) *Attorney, Agent, or Firm* — Wenderoth, Lind & Ponack L.L.P.

(57) ABSTRACT

A magnesium-based medical device which can adjust a degree of corrosion within a wide range of period such that the device can maintain a sufficient strength only during a desired period and disappears within a desired period thereafter and a manufacturing method thereof are provided. A magnesium-based medical device of the present invention is a magnesium-based medical device in which a base material is made of magnesium or a magnesium alloy, wherein a corrosion-resistant film is formed on a surface of the base material, and variation in surface hardness of the formed corrosion-resistant film in the in-plane direction is less than 21 in terms of a dispersion value of Vickers hardness.

5 Claims, 22 Drawing Sheets

(51) Int. Cl.
  *A61L 27/32* (2006.01)
  *A61L 27/58* (2006.01)
  *C23C 22/22* (2006.01)

(56) References Cited

U.S. PATENT DOCUMENTS

| | | | |
|---|---|---|---|
| 5,164,187 A * | 11/1992 | Constantz et al. | 424/423 |
| 6,207,218 B1 | 3/2001 | Layrolle et al. | |
| 2005/0079088 A1 | 4/2005 | Wirth et al. | |

FOREIGN PATENT DOCUMENTS

| | | |
|---|---|---|
| JP | 2002-28229 | 1/2002 |
| JP | 2004-160236 | 6/2004 |
| JP | 2005-518830 | 6/2005 |
| WO | 2007-058276 | 5/2007 |

OTHER PUBLICATIONS

English language Abstract of JP 2002-028229 having a publication date of Jan. 29, 2002.

Hideyuki Kuwahara et al., "Potential of Magnesium Artificial Bone", The Latest Trend in Magnesium Alloys, Kinzoku, Jul. 1, 2001, vol. 71, No. 7, pp. 656-660, ISSN:0368-6337 w/English translation.

Sachiko Ono et al., "Growth Behavior of Hydroxy-Apatite Layer on Magnesium Surfaces", Abstracts of the Meeting of Japan Institute of Light Metals, Oct. 20, 2005, vol. 109th, pp. 67 and 68.

Matsufumi Takaya et al., "Application of Magnesium to Biomaterials for Hard-Tissue", Keikinzoku, Jul. 30, 2000, vol. 50, No. 7, pp. 343-347, ISSN:0451-5994.

* cited by examiner

MAGNESIUM-BASED MEDICAL DEVICE AND MANUFACTURING METHOD THEREOF

TECHNICAL FIELD

The present invention relates to a magnesium-based medical device and a manufacturing method thereof.

BACKGROUND ART

Conventionally, a metallic medical device which is used in general remains in a body unless the medical device is removed by an operation or the like after being embedded in the body. Depending on applications, it is desirable that such a metallic medical device maintains a mechanical strength during a period that peripheral tissues are recovered, and is degraded and disappears without requiring an operation after the recovery of the peripheral tissues.

A magnesium material shows high corrosion rate in an environment where chloride ions are present and hence, the use of the magnesium material as a general-purpose-use material such as parts of transportation equipment or household appliances is limited. On the other hand, the magnesium material shows low harmful property to a living body, and is corroded, is degraded and disappears at an extremely high speed in an approximately neutral aqueous solution containing chloride ions such as a body fluid. Accordingly, the magnesium material is expected to be used as a medical biodegradation metallic material which is gradually degraded and absorbed after being embedded in a living body, so that the development of the magnesium material has been under way (see patent documents 1 and 2).

Depending on a kind of a device or a condition of an affected part, a strength holding period which the device is required to satisfy varies in an extremely wide range. For example, with respect to a blood vessel treatment device such as a stent, it is desirable that the device maintains a strength for a period of five months to six months necessary for repairing a narrowed part of a blood vessel, and the degradation of the whole device is almost finished within one week to twelve weeks after the vessel is repaired. This is because when the stent remains in the blood vessel even after the blood vessel wall is repaired, due o the mechanical stimulation and chemical irritation which the stent continuously contacts to the blood vessel wall, vascular endothelial cells are excessively grown thus causing restenosis of the blood vessel whereby the disappearance of the stent after repairing of the blood vessel is extremely important.

On the other hand, with respect to a fracture fixation device, it is desirable that the device supports a load during three months to one year until fracture is cured and, thereafter, the degradation of the whole device is almost finished within eight month to five years.

In this manner, along with the degradation and disappearance of the device after the fracture is cured, a load is gradually applied to a cured bone and hence, it is possible to suppress the load interception which is a phenomenon that the device supports the load in place of the bone. This leads o the suppression of re-fracture which occurs due to bone absorption (thinning of bone) attributed to the load interception. Further, it is unnecessary to perform an operation for taking out the device after the fracture is cured and hence, a burden imposed on a patient can be reduced. In this manner, the strength holding period which the device is required to satisfy varies in a wide range, and may be a long period of several months or more in some cases.

Accordingly, it is considered desirable if it could be possible to control the progress of degradation during a period in which the strength holding is required and a following period in which degradation progresses. However, in case of the biodegradable magnesium material proposed in patent document 1, for example, the degradation period is controlled corresponding to a size of device. Accordingly, in a living body where the degradation of the device starts immediately after embedding of the magnesium material and, at the same time, a space in which the device is to be embedded is limited, there may be a case that the device having a necessary size is not applicable whereby, it is substantially impossible to properly use the magnesium material as a device which is required to hold a strength for a particularly long period.

Further, with respect to a biodegradable magnesium material which inventors of the present invention proposed in patent document 2, the magnesium material is configured to control a strength-ductility balance of the material and a degradation speed of the material in a living body to desired values based on the composition of the material or a control of the internal structure of the material. For example, the degradation speed can be controlled by controlling a kind and the concentration of an adding element.

However, the control of the degradation speed due to the formation of an alloy using an adding element is limited and hence, the adjustment of the degradation period in a wide range is difficult. That is, the concentration of the adding element in the alloy is dependent on and defined by a desired strength-ductility balance and hence, the limitation of the adjustment range of corrosion resistance is inevitable.

Patent document 1: JP-A-2004-160236
Patent document 2: International Publication WO2007/58276 brochure

DISCLOSURE OF THE INVENTION

Problem to be Solved by the Invention

The present invention has been made in view of the above-mentioned circumstances, and it is an object of the present invention to provide a magnesium-based medical device and manufacturing method thereof which can overcome the drawbacks of the related art, and can adjust a degree of corrosion within a wide range of period such that the device can maintain a sufficient strength only during a desired period and disappears within a desired period thereafter.

Means for Overcoming the Problem

The present invention includes the following technical features which can overcome the above-mentioned drawbacks.

First technical feature: A magnesium-based medical device in which a base material is made of magnesium or a magnesium alloy, wherein a corrosion-resistant film is formed on a surface of the base material, and variation in surface hardness of the formed corrosion-resistant film in the in-plane direction is less than 21 in terms of a dispersion value of Vickers hardness.

Second technical feature: The magnesium-based medical device of the first technical feature, wherein the variation in surface hardness of the formed corrosion-resistant film in the in-plane direction is less than 12 in terms of the dispersion value of Vickers hardness.

Third technical feature: The magnesium-based medical device of the first technical feature, wherein the variation in surface hardness of the formed corrosion-resistant film in the in-plane direction is less than 10 in terms of the dispersion value of Vickers hardness.

Fourth technical feature: The magnesium-based medical device of the first technical feature, wherein the variation in surface hardness of the formed corrosion-resistant film in the in-plane direction is less than 8 in terms of the dispersion value of Vickers hardness.

Fifth technical feature: The magnesium-based medical device of the first technical feature, wherein the variation in surface hardness of the formed corrosion-resistant film in the in-plane direction is less than 7 in terms of the dispersion value of Vickers hardness.

Sixth technical feature: The magnesium-based medical device of any one of the first to fifth technical features, wherein the corrosion-resistant film contains calcium phosphate.

Seventh technical feature: A manufacturing method of the magnesium-based medical device according to any one of the first to sixth technical features, being characterized in that, in a state that the base material is immersed in a solution in which components for forming the corrosion-resistant film are dissolved, a flow of the solution whose flow speed is controlled relative to the surface of the base material thus depositing the corrosion-resistant film on the surface of the base material.

Eighth technical feature: The manufacturing method of the magnesium-based medical device according to the seventh technical features, wherein a degree of variation in surface hardness of the formed corrosion-resistant film in the in-plane direction is controlled by controlling the flow speed of the solution relative to the surface of the base material.

Ninth technical feature: The manufacturing method of the magnesium-based medical device according to the seventh or eighth technical feature, wherein the base material is immersed in a solution which contains phosphorous ions and calcium ions thus forming the corrosion-resistant film containing calcium phosphate on the surface of the base material.

The inventors of the present invention have found that although it is difficult to control a corrosion resistance period with respect to the corrosion resistance in a living body only when the corrosion-resistant film is simply formed, the smaller the variation in hardness of the film the more the corrosion resistance period can be prolonged, and have arrived at the present invention based on such finding.

Advantage of the Invention

According to the magnesium-based medical device of the present invention, a degree of corrosion resistance can be adjusted in a wide range of period so that the device can maintain a sufficient strength for a desired period and disappears after a desired period.

Further, by forming the corrosion-resistant film which contains calcium phosphate, when the magnesium-based medical device is embedded in a periphery of the bone tissue, the formation of a bone is accelerated by the calcium phosphate film thus enhancing the bonding property of a material and the bone. The surface on which calcium phosphate is deposited exhibits high soft tissue compatibility and hence, the device exhibits high soft tissue compatibility when embedded in a blood vessel.

Further, it is possible to use the magnesium-based medical device as a regenerative medical device which replaces a bone which is regenerated along the decomposition and absorption of a magnesium material such as an artificial bone or a bone plate embedded in a defective part of the bone.

According to the manufacturing method of the magnesium-based medical device of the present invention, it is possible to adjust the corrosion resistance of the film in conformity with a corrosion resistance period and a disappearance period which are determined based on a material of the base, a kind, a size and a purpose of use of the device used, the individual specificity of a living body and the like.

Further, since a voltage or an electric current is not applied to the base material in forming the corrosion-resistant film, it is possible to form a desired film over the whole surface of the base irrelevant to a shape of the device. Further, since the relative speed between the base material and the solution is controlled, it is possible to change the homogeneity of the film in a versatile manner.

BEST MODE FOR CARRYING OUT THE INVENTION

Figure 1:
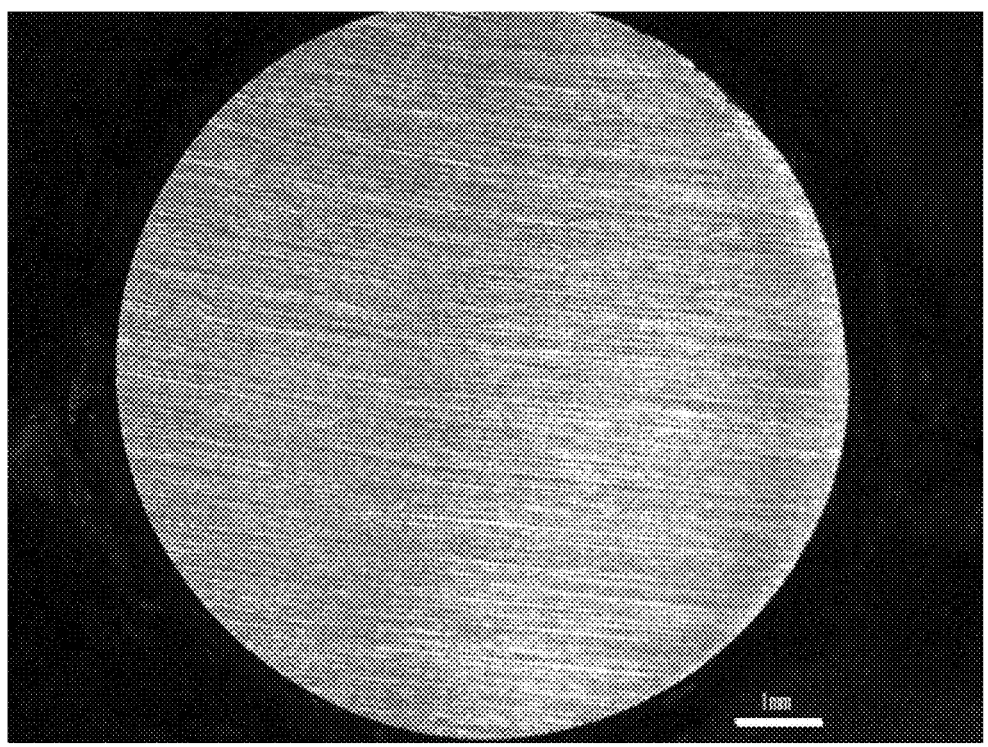
FIG. 1 A photograph showing a surface of untreated pure magnesium which is polished.
Figure 2:
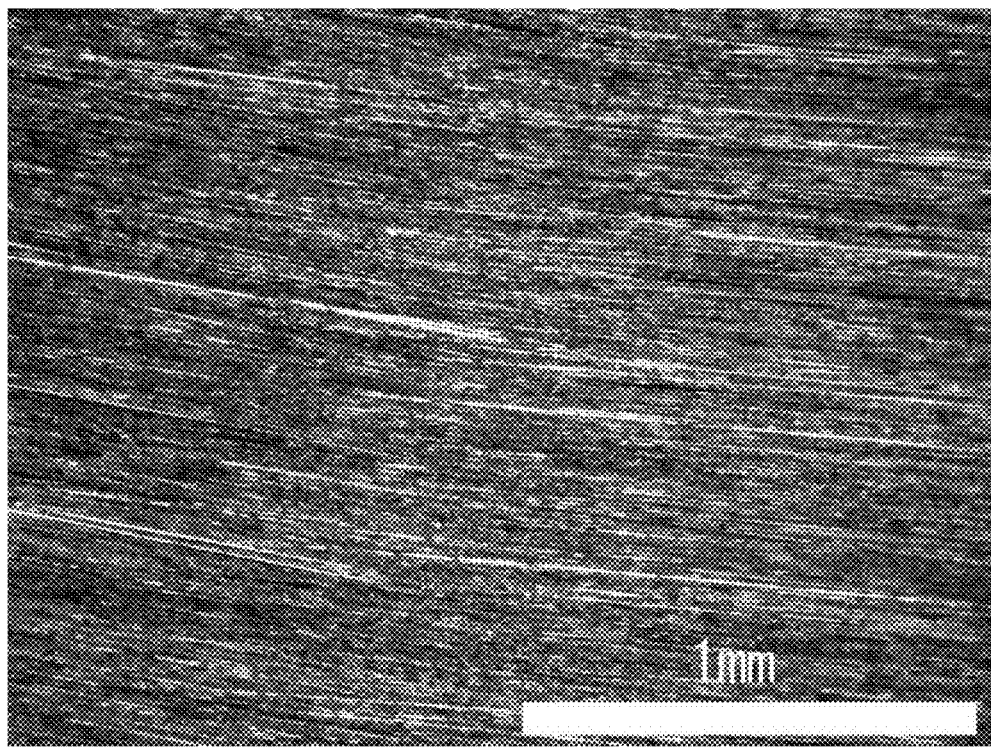
FIG. 2 A five-time enlarged photograph of the surface of the pure magnesium shown in FIG. 1.

The present invention which has the above-mentioned technical features is explained in conjunction with embodiments hereinafter.

A base material of a medical device according to the present invention is directed to, in addition to pure magnesium, magnesium alloys which contain Mg as a main component and further contain a second component. The base material, in general, contains the second component with a quantity not more than ⅓ of the limit concentration of the second component element for its solid solution in magnesium. Also in such a case, it is needless to say that the inclusion of inevitable impurities is allowable. For example, the base material is allowed to contain impurities of not more than 0.05 atomic %.

The base material preferably contains a quantity of second component such that the solid solution limit concentration of the second component as an element is not more than ¼ with respect to magnesium. As a specific example of the element which constitutes the second component, it may be possible to name Au, Ir, Mn, Zr, Bi, Co, Zn, Ga, Ag, Al, Li, Ce, Pr, La, Th, Nd, Ca, Yb, Rb, Y, Gd, Dy, Tm, Er, Lu, Sc, In or the like excluding elements which form substantially no solid solutions with magnesium or elements which evidently have damaging property to a living body.

Further, a grain size of the magnesium alloy is not more than ¼ of a minimum portion of the magnesium alloy. The alloy can acquire desired dynamic characteristics such as strength, work hardening property, ductility by controlling a kind, quantity and a grain size of the second component.

With respect to the configuration of the base material such as a shape and a size of the base material, the base can take any arbitrary configuration corresponding to an object of an application.

According to the present invention, as a method of controlling corrosion of the base material made of magnesium or the magnesium alloy, by generating a flow of a treatment solution on a surface of the base plate, it is possible to form a film in such a manner that variation in hardness of the base material, that is, variation in the constitution or the structure of the film can be adjusted.

The film formed on the surface of the base material by the method of the present invention functions as a corrosion-resistant film of the base material, and can suppress the degradation and the dissolution of the base material in an environment. Further, when the method of the present invention is applied to a medical biodegradable magnesium material, a period from a point of time immediately after embedding of the base material in a living body to a point of time that the degradation of the base material starts can be prolonged and hence, the base material can surely maintain an original strength during that period.

As a method for controlling a flow speed of the solution on the surface of the base material, for example, a method which rotates the base material in a solution, a method which oscillates the base material vertically or laterally in a solution, or a method which stirs a solution or the like is named. A flow speed of a solution on the surface of the base material depends on a relative speed between the surface of the base material and the solution, and does not depend on a method which moves the base material. Accordingly, an arbitrary method can be used depending on a size or a shape of the device.

The flow speed and the treatment time of the solution can be suitably changed corresponding to the composition of the base material, and corrosion resistance, biocompatibility or the like of the desired film. The larger the flow speed, the more the homogeneity of the film to be formed is improved. Usually, the longer the treatment time, the larger a thickness of the film becomes.

The method of the present invention is applicable irrespective of the composition or the structure of the base material and hence, the base material can maintain a desired strength-ductility balance and the like without incurring the rapture of the composition or the structure thereof.

According to the method of the present invention, the surface film is formed along with the deposition of a solute and hence, the structure, the thickness, the composition and the like of the film can be changed in a versatile manner whereby corrosion resistance and the biocompatibility of the film can be adjusted.

The composition, the configuration and the like of the film can be controlled in a versatile manner corresponding to conditions such as a flow speed of a solution, a treatment time, a kind and concentration of a using treatment solution, for example.

With respect to a treatment solution or an environment, it is desirable that the solution contains an element which contributes to the improvement of corrosion resistance of magnesium material. As a specific example of a component of the treatment solution used in the present invention, a salt of a phosphoric acid, a silicic acid or an aluminic acid, and a salt or a complex of calcium or the like can be named. To be more specific, for example, sodium biphosphate, dibasic sodium phosphate, sodium silicate, sodium aluminate, aluminum hydroxide, calcium chloride, a calcium complex and the like can be named. These elements can be used in a single form or two or more kinds of elements may be used in combination.

Besides a case where a content is deposited due to bonding of ions in a solution such as calcium phosphate, for example, when a solution which contains Al ions is used, Al can be taken into a film as oxide of Al or a composite oxide of Al and Mg. In this manner, by changing the condition such as composition or concentration of a treatment solution, for example, it is possible to allow a film to take an element in a solution thereinto.

According to the method of the present invention, with the use of the solution which contains phosphate ions and calcium ions, calcium phosphate is deposited on the surface of the base material and is taken into the base material. It is possible to adjust a quantity of calcium phosphate taken into the film based on concentration of phosphate ions and concentration of calcium ions in the solution, a treatment time and a flow speed of the solution.

As such a treatment solution, for example, it is possible to use a calcium phosphate solution which is prepared by removing chloride ions which promote dissolution of magnesium while using a pseudo body fluid. To be more specific, a Hank's balanced salt solution or a culture medium which is prepared using phosphate and calcium can be exemplified as the treatment solution, and these Hank's balanced salt solution and the culture medium are useful as solutions which can easily deposit calcium phosphate.

Calcium phosphate which is deposited on the surface of the base material changes, due to taking magnesium into the structure thereof, the composition and the structure of the film based on a flow speed of a solution and a treatment time. Further, as the homogeneity of the film becomes higher and the structure of the film becomes denser, the corrosion resistance of the base material becomes higher and hence, it is possible to adjust a degradation-suppressed time of the base material at an initial stage of embedding the device into a living body within a wide range of period.

Further, the composition and the structure of calcium phosphate in the film directly influence biocompatibility in a living body and hence, biocompatibility can be controlled by controlling a treatment time.

Calcium phosphate improves bone conduction between a bone and a material by promoting the formation of the bone, and also exhibits favorable affinity with a vascular endothelial cell. Due to such a characteristic, the device which exhibits extremely high biocompatibility on a treated surface thereof can be realized. Accordingly, when the medical biodegradable device which is treated in such a manner is embedded in a living body, a surface of the device is suitably bonded to a peripheral tissue and exhibits favorable affinity with cells of the peripheral tissue and hence, the surface of the device exhibits high biocompatibility. Accordingly, for example, there is no formation of thrombus and hence, it is expected that curing of the peripheral tissue starts from an initial stage of embedding and curing is finished early.

Further, recently, the medical treatment which promotes curing of an affected part by supplying a medicament to the affected part from a surface of a living body material is carried out. In taking calcium phosphate which is liable to absorb protein or the like into a surface, when the medicament or protein is added to a treatment solution, it is possible to take these materials into a film. Accordingly, it is also possible to manufacture a medical device which holds various kinds of medicaments necessary for speeding up curing. Further, with the coupled use of a conventional slow releasing technique in which a medicament is contained in calcium phosphate, it is also possible to release the medicament slowly.

For example, when the device is used for fracture fixation, considered is a medical treatment in which protein or the like which is a bone growth factor is taken into a film, protein or the like is slowly released from a surface of the film after the device is embedded in a living body thus promoting the formation of a bone and eventually promoting curing of fracture.

Further, when the device is a stent, by allowing the film to hold a medicament for preventing restenosis which occurs due to abnormal growth of vascular endothelial cells caused by continuous mechanical stimulation to a blood vessel wall from the stent, a medicament is supplied from a surface of the stent thus providing the medical treatment which prevents the abnormal growth of vascular endothelial cells.

Further, a blood vessel wall having an affected part exhibits a low strength and low resiliency compared to a normal blood vessel wall and hence, the blood vessel wall having the affected part cannot recover the strength and resiliency of the normal blood vessel wall when the stent merely expands the blood vessel wall by pushing. However, according to the present invention, it is also possible to provide the medical treatment which slowly releases a medicament for promoting the repair of the blood vessel wall from a surface of the stent.

Further, for example, by embedding a device which carries a medicament thereon (a medicament slow releasing medical device) in a bone of a patient suffering from osteoporosis, it is possible to provide the medical treatment which promotes the increase of bone quantity by slowly releasing the medicament from the device.

Hereinafter, the present invention is explained in further detail in conjunction with examples. However, the present invention is not limited to these examples in any ways.

EXAMPLES

Example 1

As a base material, pure magnesium (purity: 99.9%, grain size: 1 μm) whose surface is polished is used.

Figure 18:
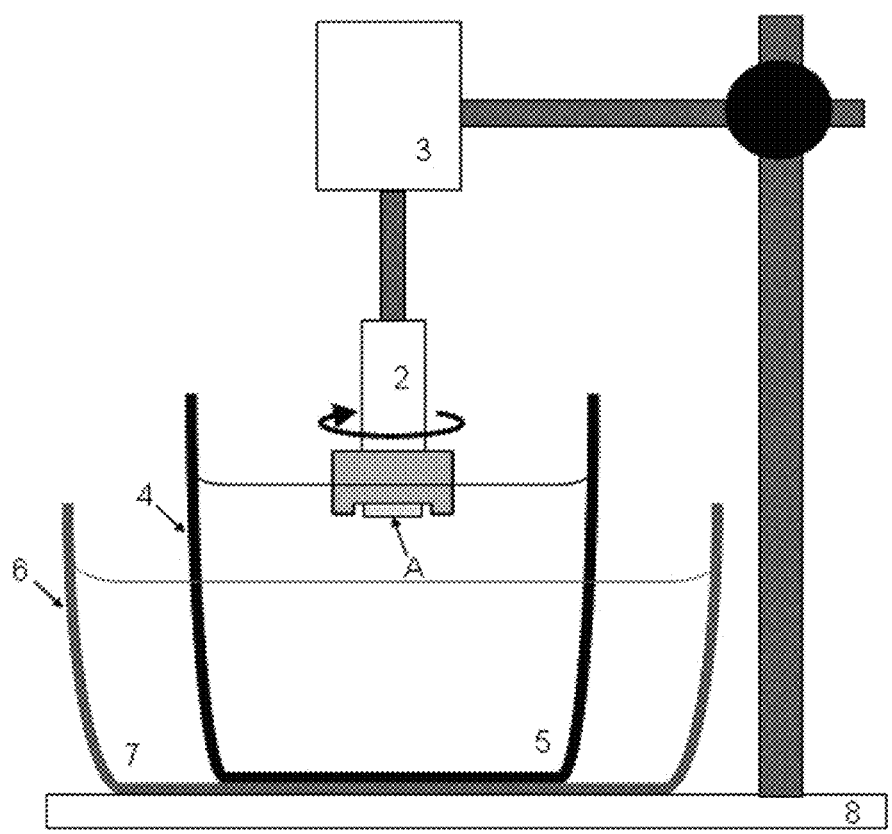
FIG. 18 A longitudinal cross-sectional elevation view showing a state in which the base material is rotated while being immersed in the solution.

As shown in FIG. 18, a base material (A) is mounted on a rotation device. The base material (A) is immersed in a phosphoric acid buffer solution which contains calcium ion (5) at a temperature of 37° C. while rotating the base material (A) at rotation speeds of 0 rpm, 30 rpm, 60 rpm, 120 rpm, 1440 rpm and 2880 rpm. Thereafter, the base material (A) is immersed for 10 minutes thus forming a film containing calcium phosphate on a surface of the base material (A).

In the rotation device shown in FIG. 18, a specimen rotating jig (2) which fixes the base material (A) thereto by an adhesive agent is fixed to a lower end of a main shaft of a motor (3).

A quantity of the solution (5) sufficient to immerse the specimen rotating jig (2) in the solution (5) is stored in a container (4). The container (4) is housed in the inside of a temperature controlled water bath (6) so as to hold the solution (5) at a predetermined temperature (7) in the temperature controlled bath (6). A support strut (8) is provided for holding the motor (3) at a height which allows the rotation of the base material (A) in the solution (5).

Here, a surface of the base material described hereinafter means a lower surface of the base material (A) in FIG. 18. The rotation speeds of the base material (A) of 0 rpm, 30 rpm, 60 rpm, 120 rpm, 1440 rpm, and 2880 rpm correspond to linear flow speeds of 0 m/s, 0.02 m/s, 0.04 m/s, 0.08 m/s, 1 m/s and 2 m/s respectively.

In this embodiment, as a method of controlling a flow speed of the solution on the surface of the base material, a method which rotates the base is adopted.

Figure 3:
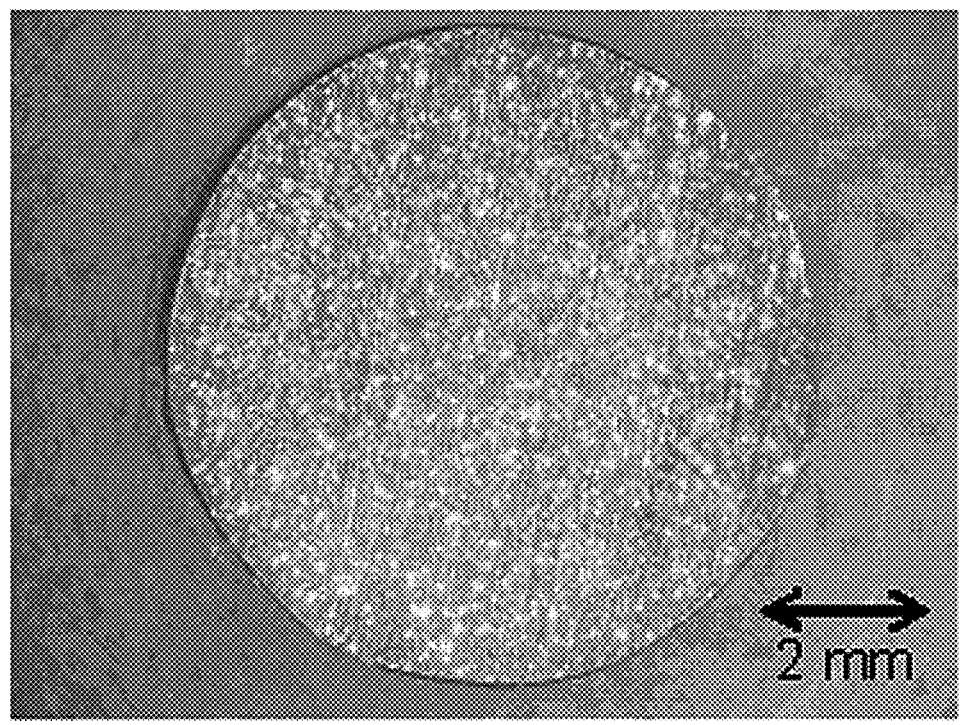
FIG. 3 A photograph showing a surface of pure magnesium treated at a rotational speed of 0 rpm in an example 1.
Figure 4:
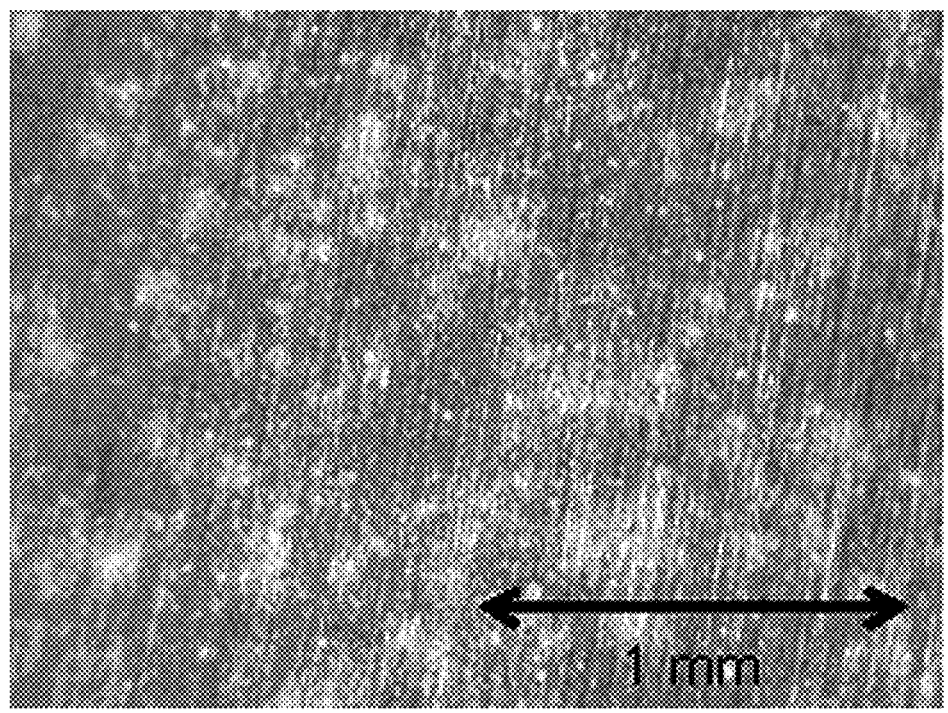
FIG. 4 A five-time enlarged photograph of the surface of pure magnesium shown in FIG. 3.
Figure 5:
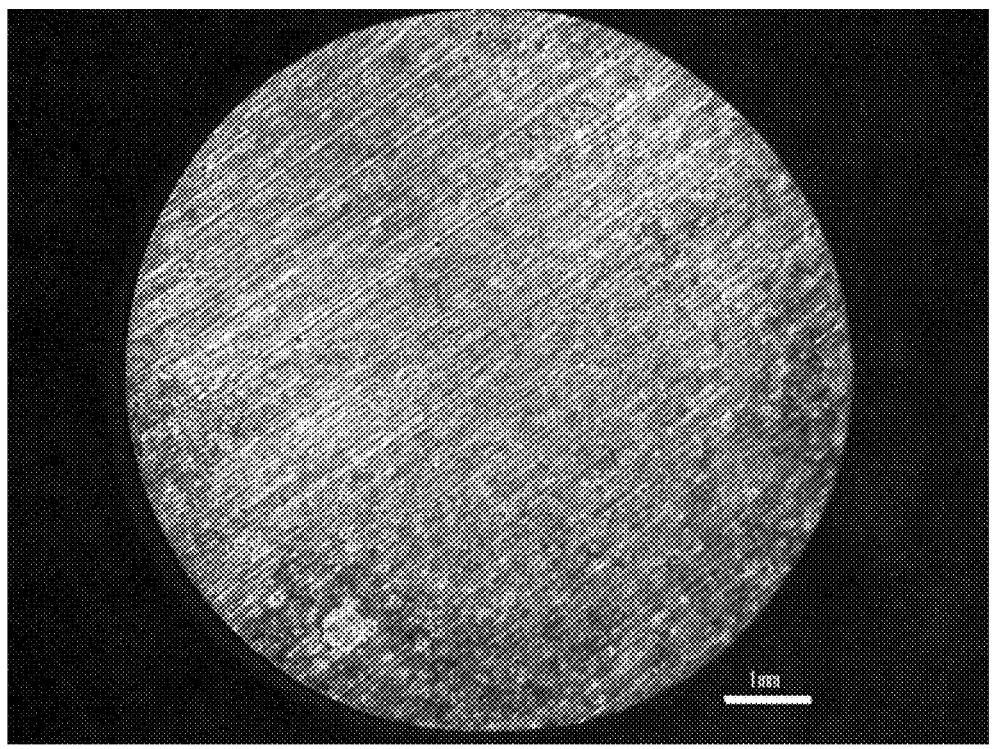
FIG. 5 A photograph showing a surface of pure magnesium treated at a rotational speed of 30 rpm in the example 1.
Figure 6:
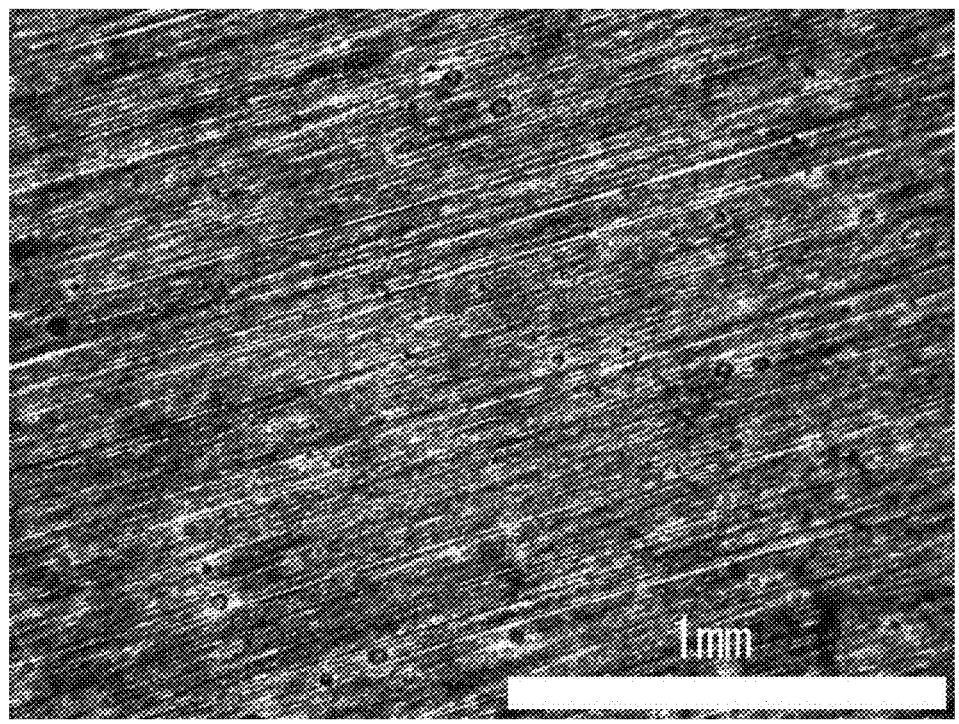
FIG. 6 A five-time enlarged photograph of the surface of pure magnesium shown in FIG. 5.
Figure 7:
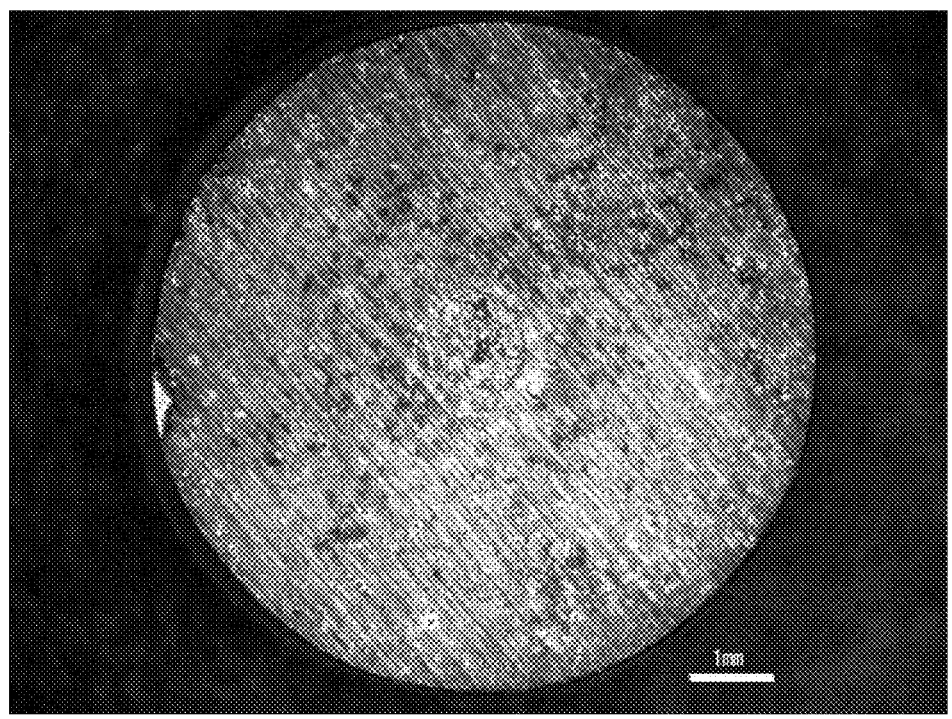
FIG. 7 A photograph showing a surface of pure magnesium treated at a rotational speed of 60 rpm in the example 1.
Figure 8:
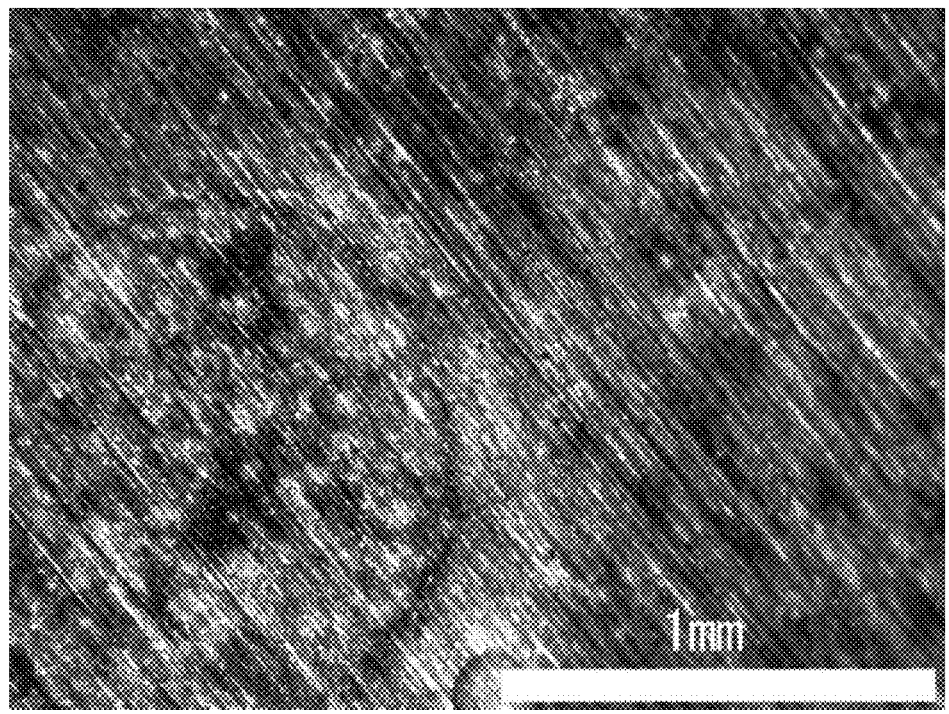
FIG. 8 A five-time enlarged photograph of the surface of pure magnesium shown in FIG. 7.
Figure 9:
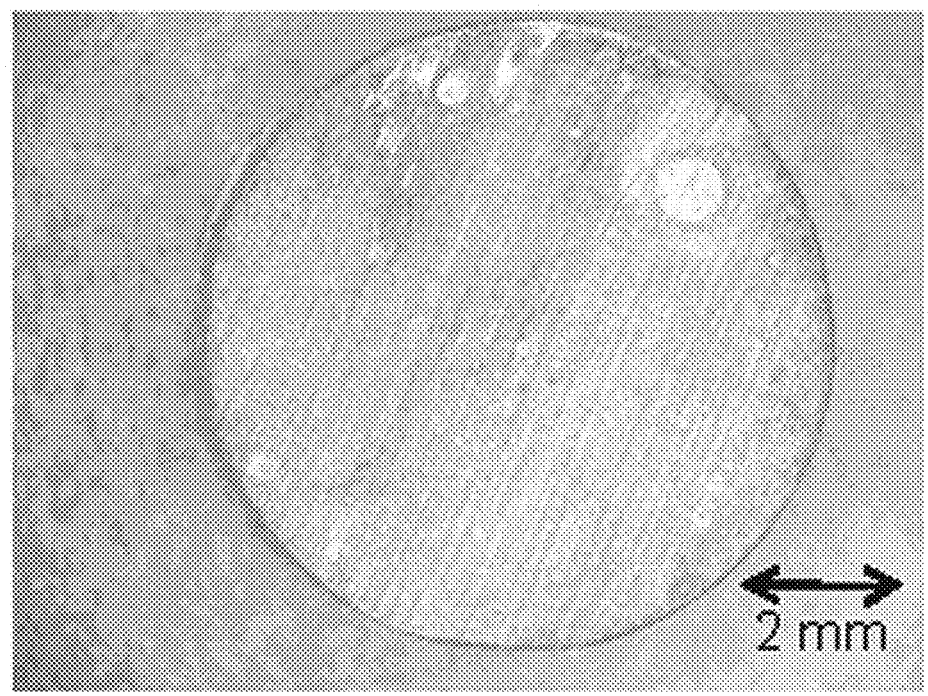
FIG. 9 A photograph showing a surface of pure magnesium treated at a rotational speed of 120 rpm in the example 1.
Figure 10:
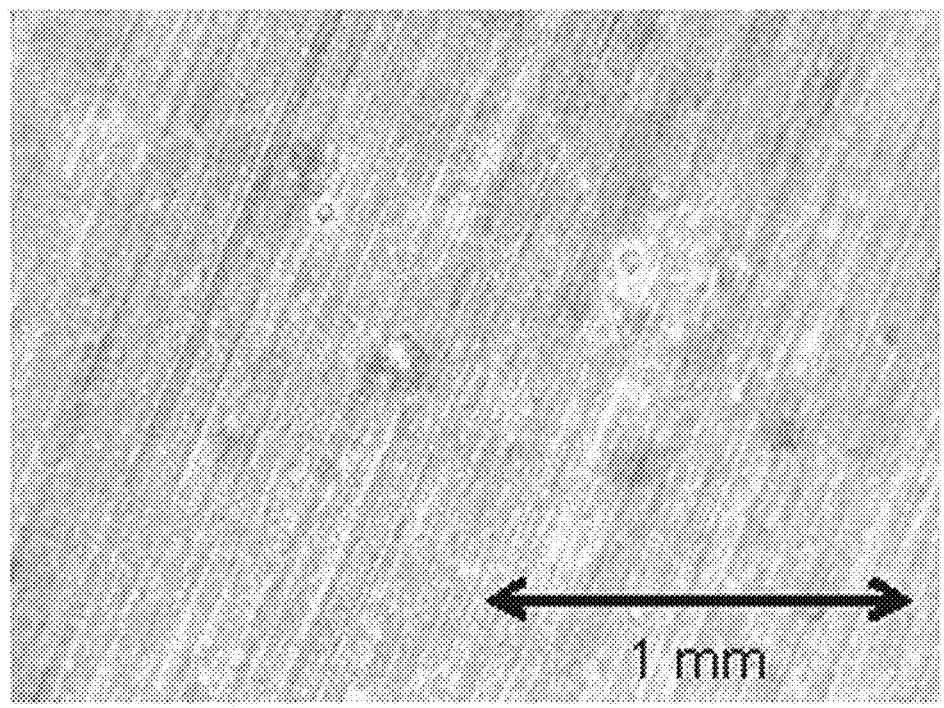
FIG. 10 A five-time enlarged photograph of the surface of pure magnesium shown in FIG. 9.
Figure 11:
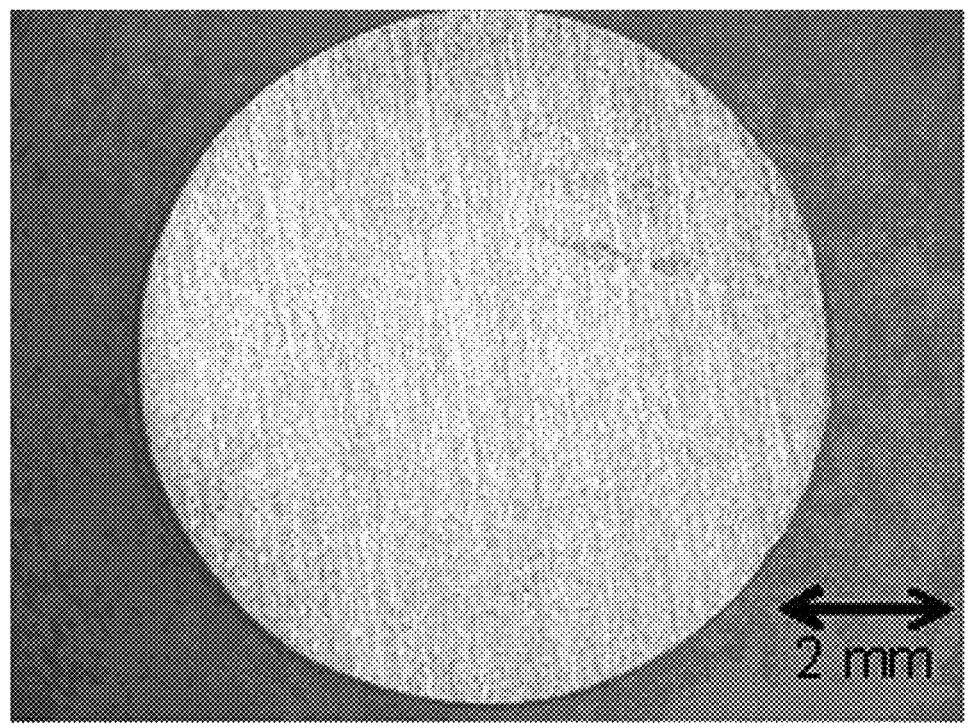
FIG. 11 A photograph showing a surface of pure magnesium treated at a rotational speed of 1440 rpm in the example 1.

FIG. 1 to FIG. 14 show photographs of the appearance of surfaces treated at respective rotation speeds. The surface (FIG. 3, FIG. 4) treated at the rotation speed of 0 rpm (not rotated) exhibits the appearance in which white spots are scattered in a gray background as a whole and hence, it is expected that calcium phosphate is not homogeneously deposited.

The surface (FIG. 5, FIG. 6) treated at the rotational speed of 30 rpm exhibits a non-homogeneous and uneven appearance, wherein a large number of indentations of several microns are formed.

The surface (FIG. 7, FIG. 8) treated at the rotation speed of 60 rpm exhibits the appearance substantially equal to the appearance when the surface is treated at the rotation speed of 30 rpm. However, the number of depressions of several microns is smaller than the number of depressions when the surface is treated at the rotation speed of 30 rpm.

On the other hand, the surface (FIG. 9, FIG. 10) treated at the rotation speed of 120 rpm exhibits the appearance in which the whole surface is covered with a white film, and white spots are locally observed on the surface in the low-magnification observation. In the high-magnification observation (FIG. 10), gray and white spots are locally observed on the white surface. To compare the surface treated at the rotation speed of 120 rpm and the surface treated at the rotation speed of 0 rpm, it is considered that calcium phosphate is deposited more homogeneously on the surface treated at the rotation speed of 120 rpm.

Figure 12:
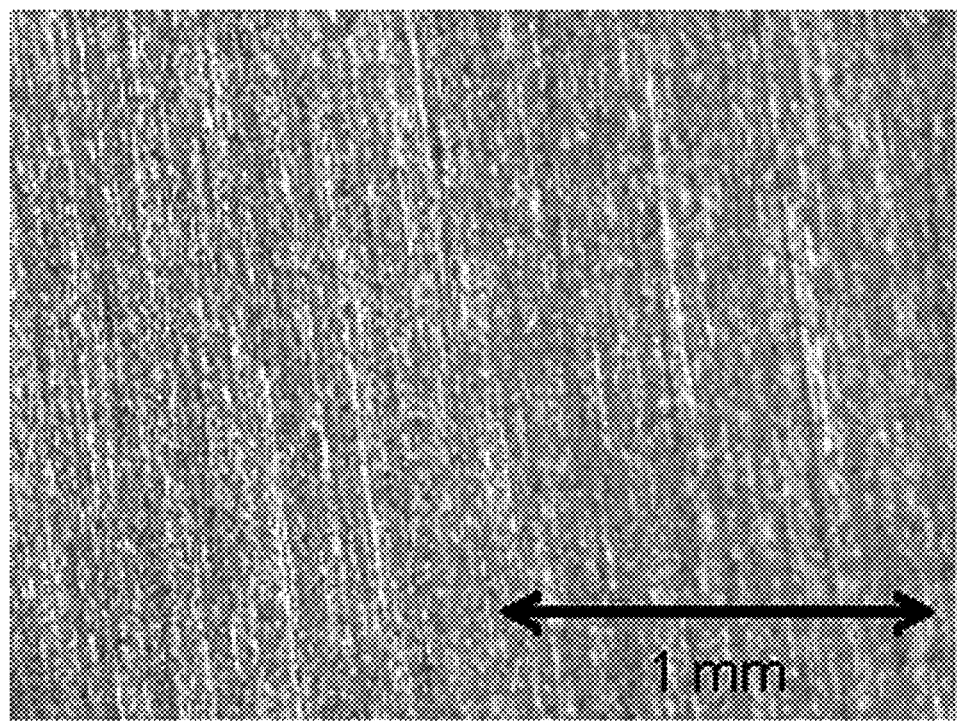
FIG. 12 A five-time enlarged photograph of the surface of pure magnesium shown in FIG. 11.
Figure 13:
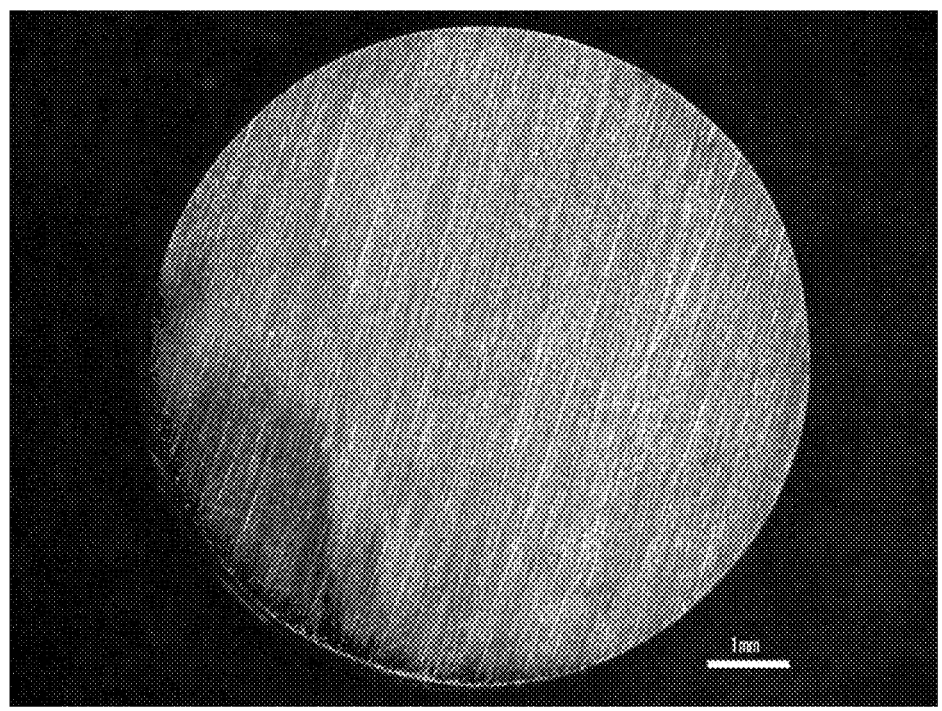
FIG. 13 A photograph showing a surface of pure magnesium treated at a rotational speed of 2880 rpm in the example 1.
Figure 14:
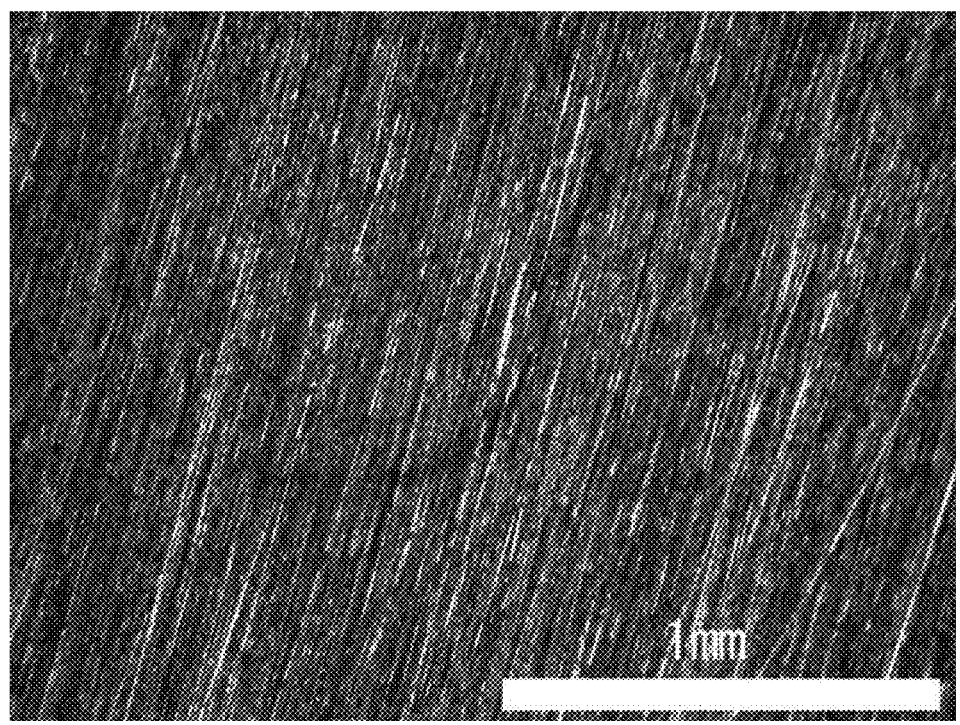
FIG. 14 A five-time enlarged photograph of the surface of pure magnesium shown in FIG. 13.

The surface (FIG. 11, FIG. 12) treated at the rotation speed of 1440 rpm exhibits the appearance in which the whole surface is covered with a white film substantially homogeneously, and non-homogeneous portion is not observed even in the high-magnification observation (FIG. 12). It is considered that calcium phosphate is homogeneously deposited when the surface is treated at the rotation speed of 1440 rpm.

From these results, it is evident that the larger the rotation speed of the base, that is, the larger the flow speed of the treatment solution, calcium phosphate is deposited uniformly and homogeneously.

Further, due to the difference in the appearance of the formed film, the composition and the structure of calcium phosphate are changed corresponding to the flow speed of the treatment solution. When the surface (FIG. 13, FIG. 14) is treated at the rotation speed of 2880 rpm, in the observation of the whole surface of the base material, black portions are observed at an edge of a disk. On the other hand, in the high-magnification observation, the homogeneous surface film which is free from indentations and non-homogeneous portions is formed.

Figure 19:
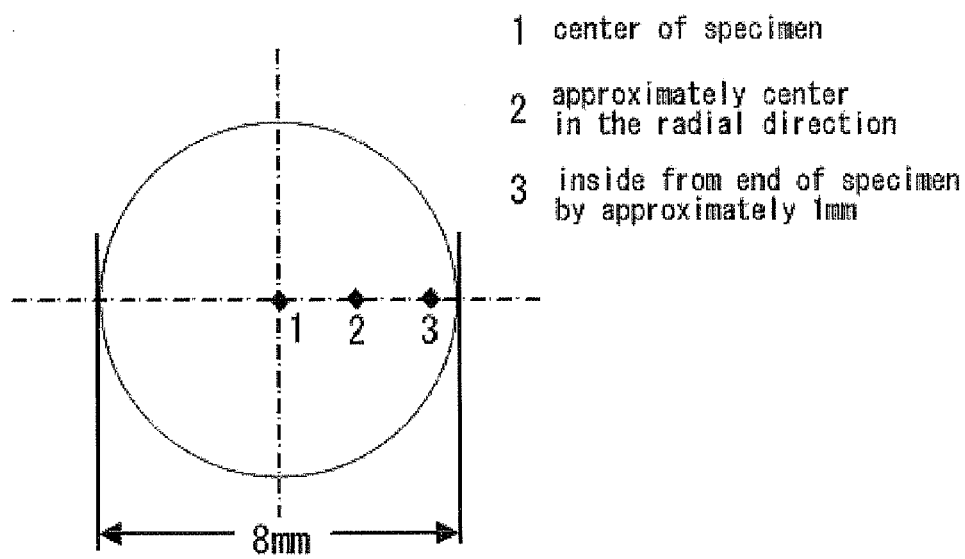
FIG. 19 A plan view of a treated surface indicating measuring points of a Vickers hardness test in an example 1.

To determine these surface conditions in a more scientific manner, Vickers hardness of the surface is measured at three points shown in FIG. 19 where a measurement distance between the points is set to 4 mm, and an average value of the measured values is set as surface hardness of the base material. A result of the measurement is shown in table 1 and FIG. 17. A Vickers hardness test (JIS Z 2244) is performed using a micro-Vickers hardness meter (made by AKASHI: MVK-E), and the surface hardness is measured by setting a load of an indenter to 10 gf and a holding time to 15 seconds.

Figure 17:
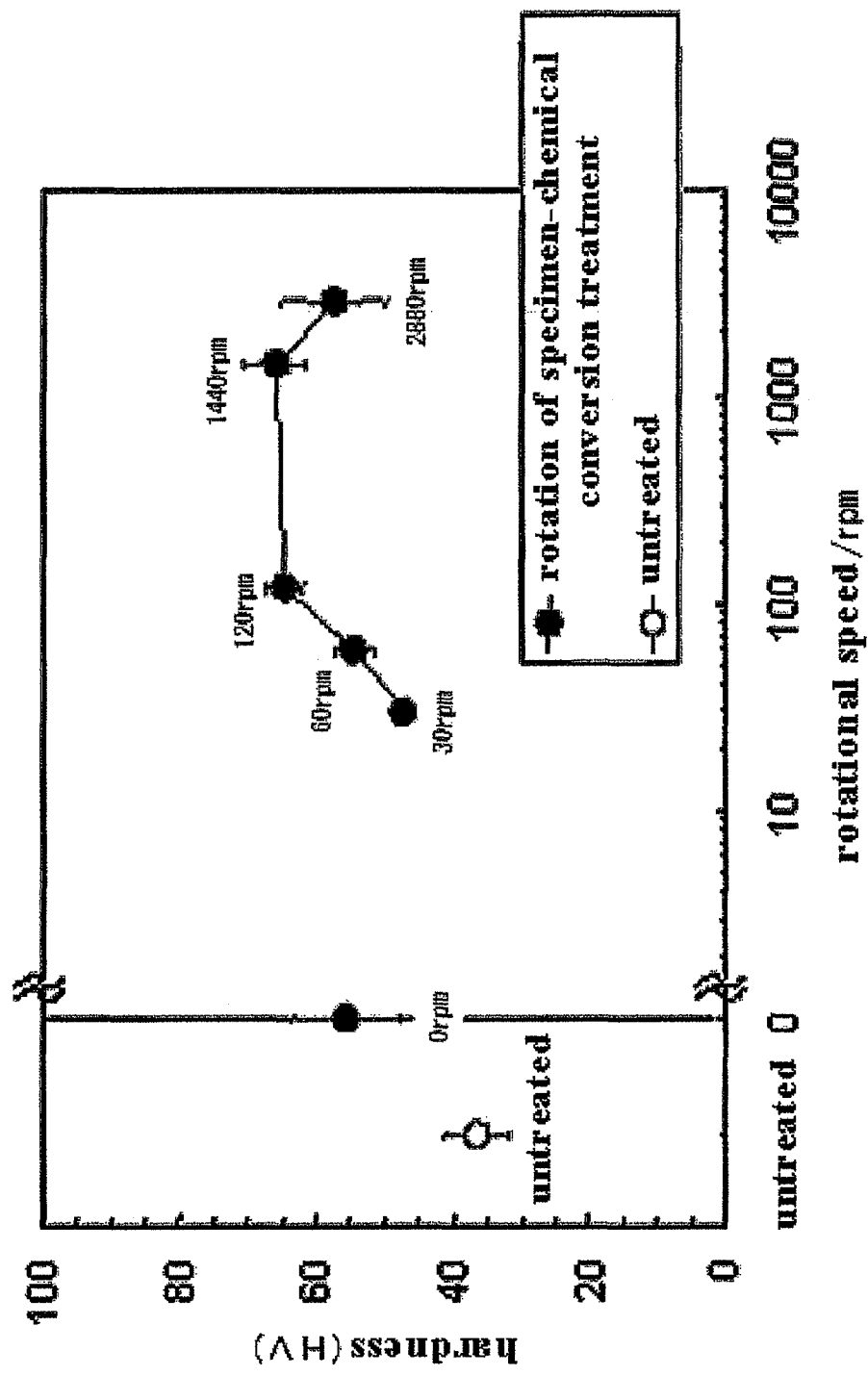
FIG. 17 A graph showing surface hardness of a film formed on a surface of a pure magnesium which is subject to surface treatment with the rotation in a calcium phosphate solution.

As shown in following Table 1, compared to the surface hardness of the untreated surface, the surface hardness of the surface treated in the solution exhibits a large value irrespective of the rotation speed. Further, due to the rotation of the base, an error bar indicative of a standard deviation value of the hardness shown in FIG. 17 is lowered so that variation in surface hardness is decreased.

Since the variation in surface hardness is small, it is evident that the film formed by rotating the base is homogeneous in the in-plane direction. The increase of surface hardness implies that the film structure is more densified. Further, from results of examples described later, it is found that when the device is pure magnesium, the larger the surface hardness and the smaller the variation in surface hardness, the larger a dissolution quantity can be suppressed. In general, the diffusion of the magnesium ions toward a solution side from a background is suppressed due to the densification of the film and hence, it is considered that the dissolution of magnesium is suppressed when the denseness of the film is enhanced.

Example 2

[Immersion Test]

The base material which is obtained by the example 1 and deposits calcium phosphate on the surface thereof is immersed in 27.5 ml of culture medium (E-MEM+10% FBS) in the inside of an 5% $CO_2$ incubator held at a temperature of 37 C.° for 5 clays, and the determination of magnesium ions dissolved in the culture medium is performed by a xylidyl blue method.

Figure 15:
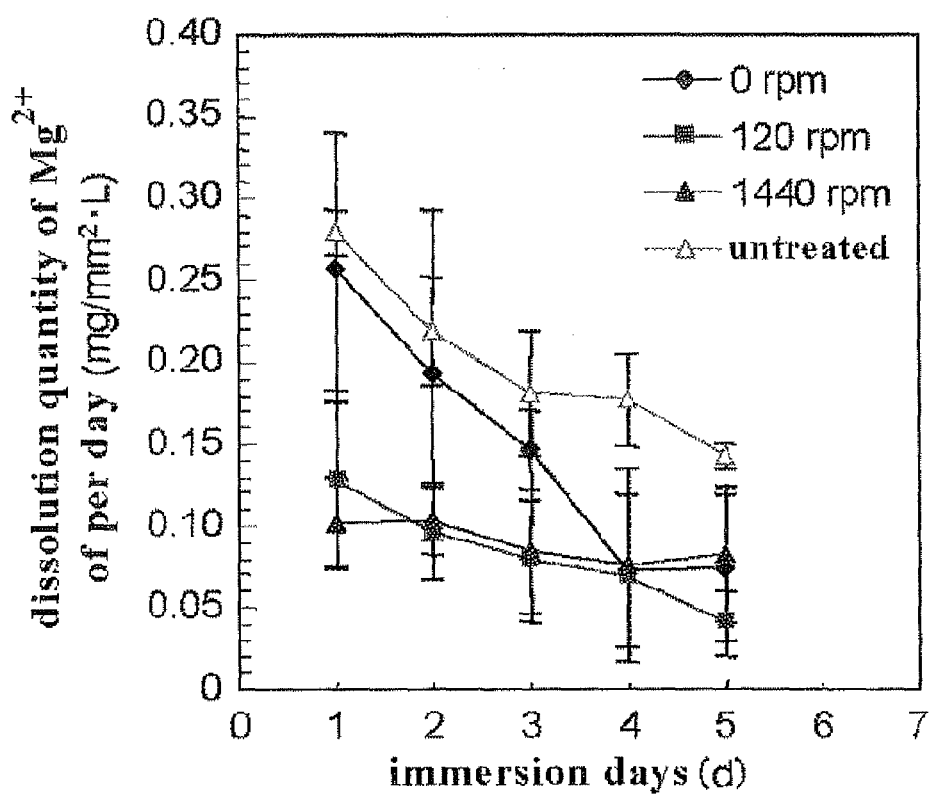
FIG. 15 A graph which exemplifies a degradation speed in a culture medium of pure magnesium whose surface is treated with the rotation at different rotational speeds.
Figure 16:
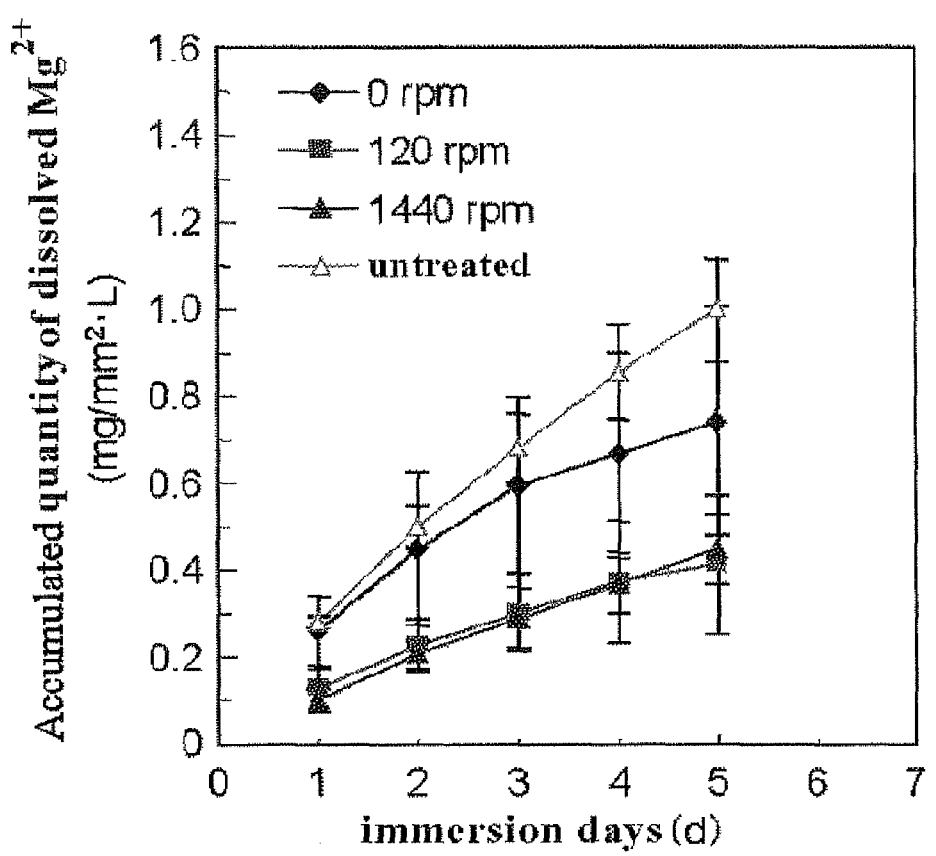
FIG. 16 A graph showing a cumulative quantity of magnesium dissolved in a culture medium from pure magnesium which is subjected to surface treatment with the rotation at different rotation speeds.

Here, the culture medium is exchanged by 15 ml for every day, and the quantification is performed using a sampled solution. A dissolution quantity of magnesium ions is shown in FIG. 15. Further, a cumulative dissolution quantity of magnesium at each immersion days is shown in FIG. 16. The base material (FIG. 1, FIG. 2) to which only polishing is applied without applying the treatment is prepared as a comparison material, and a dissolution test in the cell-culture solution is also carried out with respect to this base. The above is summarized in Table 1.

TABLE 1

| Rotation speed of specimen during treatment (rpm) | Vickers hardness (Hv) | Dissolution quantity of Mg in 1st day/ mg/mm$^2$ · L | Dissolution quantity of Mg in 5th day/ mg/mm$^2$ · L |
|---|---|---|---|
| untreated | 36.6 ± 4.6 | 0.279 ± 0.014 | 0.142 ± 0.007 |
| 0 | 55.8 ± 7.7 | 0.258 ± 0.082 | 0.075 ± 0.045 |
| 30 | 47.4 ± 1.2 | — | — |
| 60 | 54.6 ± 2.9 | — | — |
| 120 | 64.6 ± 2.7 | 0.128 ± 0.054 | 0.041 ± 0.019 |
| 1440 | 66.0 ± 4.5 | 0.102 ± 0.027 | 0.083 ± 0.042 |
| 2880 | 57.4 ± 7.7 | — | — |

Respective values in Table indicate an average value ± a standard deviation value.

The base material to which the treatment is applied with the rotation exhibits small magnesium dissolution quantity in an initial stage of immersion into culture medium compared to the base material (FIG. 3, 4) to which the treatment is applied without rotation. It is found that the film formed in a state that the base material is rotated, that is, the film formed under a control of a flow speed of the solution exhibits a large effect in the suppression of dissolution of magnesium. Further, the magnesium dissolution quantity of the base material to which the treatment is applied without rotation in an initial stage of immersion is substantially equal to the magnesium dissolution quantity of the base to which the treatment is not applied.

This result shows that the homogeneous film which is formed by controlling the flow of the solution has an effect of suppressing the degradation of magnesium material in an initial stage of immersion. The dissolution quantity of magnesium into the culture medium is decreased along with the increase of immersion days irrespective of the treatment condition of the surface of the base material.

The dissolution quantity of magnesium from the base material to which the treatment is applied with the rotation of the base material is smaller than the dissolution quantity of magnesium from the base material to which the treatment is applied without rotation of the base material until the third immersion day. However, on the fourth immersion day and thereafter, the substantially same magnesium dissolution quantity is detected irrespective of presence or non-presence of rotation of the base material during the treatment. It is found that the influence on the degradation suppressing effect due to the film exerted by the different flow speeds of the solution is conspicuous in an initial stage of immersion.

On the other hand, to compare the base material to which the treatment is applied without rotation and the untreated base material, it is found that the longer the immersion time, the more the degradation of the base material to which the treatment is applied without rotation is suppressed. Irrespective of the presence or the non-presence of the rotation of the base material during the surface treatment, a total dissolution quantity of magnesium from a surface of the magnesium material treated with the calcium phosphate solution is small.

Example 3

[Surface Composition of Magnesium-based Material which is Treated Under Controlled Solution Flow]

Out of pure magnesium materials which are prepared by the method explained in the example 1 and which deposit calcium phosphate on surfaces thereof, the surface compositions of specimens when the rotation speed during the surface treatment is set to 0 rpm, 30 rpm, 1440 rpm and 2880 rpm are measured by an energy-dispersion type X-ray analysis (EDS). The compositions of the surfaces formed at the respective rotation speeds are shown in Table 2.

TABLE 2

Composition of film obtained in mixture solution of phosphoric acid and calcium

| Rotation speed during treatment (rpm) | Concentration (at %) | | | |
|---|---|---|---|---|
| | O | Mg | P | Ca |
| 0 | 14.9 | 84.9 | 0.2 | 0.0 |
| 30 | 14.4 | 84.5 | 0.7 | 0.4 |
| 1440 | 20.8 | 77.7 | 0.8 | 0.7 |
| 2880 | 18.1 | 79.2 | 1.5 | 1.2 |

The specimens to which the treatment is applied with the rotation exhibit the high P concentration and the high Ca concentration compared to the specimen to which the treatment is applied without rotation. Further, along with the increase of the rotation speed, P concentration and Ca concentration are increased. Accordingly, it is found that when a flow speed of the solution on the surface of the base material is increased, a deposition quantity of calcium phosphate is increased. It is also found that O concentration is increased along with the increase of the rotation speed of the specimen. This suggests a possibility of the increase of a thickness of the formed film when the flow speed of the solution on the surface of the base material is increased. From these results, it is evident that an intake quantity of the film forming element from the solution can be controlled by controlling the flow speed of the treatment solution on the surface of the base material made of the magnesium-based material.

Example 4

[Dispersion of Surface Hardness of Magnesium-based Material Treated Under Solution Flow Control]

Figure 20:
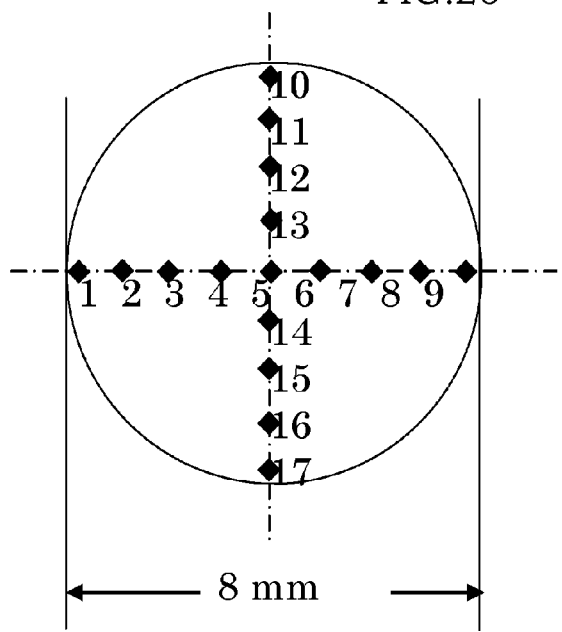
FIG. 20 A plan view of a treated surface indicating measuring points of a Vickers hardness test in an example 4.

Out of the pure magnesium materials which are prepared by the method explained in the example 1 and which deposit calcium phosphate on surfaces thereof, Vickers hardness is measured with respect to surfaces of specimens by setting the rotation speed at 0 rpm, 30 rpm, 120 rpm, 1440 rpm and 2880 rpm during the surface treatment at 17 points at measurement intervals of 1 mm as shown in FIG. 20. In a comparison example, the similar measurement is also performed with respect to a surface of an untreated material to which only polishing is applied. In a Vickers hardness test (JIS Z 2244), the measurement is made using a micro-Vickers hardness meter (made by AKASHI: MVK-E) while setting a load of an indenter to 10 gf and a holding time to 15 seconds. Table 3 shows an average±standard deviation and the dispersion of measured values. It is found from this test that the smaller the dispersion value, the smaller the variation in hardness of the surface of the specimen in the in-plane direction becomes. That is, this test shows that the formed film is homogeneous in the in-plane direction.

TABLE 3

Relationship among rotation speed, hardness of film and variation (dispersion) in hardness

| | Rotation speed of specimen during treatment (rpm) | | | | | |
|---|---|---|---|---|---|---|
| | untreated | 0 | 30 | 120 | 1440 | 2880 |
| Vickers hardness (Hv) | 43.7 ± 2.7 | 47.6 ± 4.8 | 47.1 ± 3.0 | 47.0 ± 1.2 | 46.5 ± 1.8 | 46.2 ± 3.1 |
| Dispersion | 7.0 | 21.7 | 8.7 | 1.5 | 2.9 | 9.1 |

*Each numerical value of Vickers hardness in Table indicates an average value ± standard deviation.

By carrying out the significant difference test of F distribution based on the dispersion 21.7 in hardness of the surface to which the treatment is applied at the rotational speed of 0 rpm, the significance of difference between the dispersion in hardness of the surface to which the treatment is applied with rotation and the dispersion in hardness of the surface to which the treatment is applied without rotation are determined with certain reliability. In carrying out the significant level 1% one-sided test, when the dispersion in hardness of the surface to which the treatment is applied with rotation is smaller than 6.4, it is safe to say that the dispersion in hardness of the surface to which the treatment is applied with rotation is significantly smaller than the dispersion in hardness of the surface to which the treatment is applied at the rotation speed of 0 rpm with reliability of 99%. In carrying out the significant level 5% both-sided test, when the dispersion in hardness of the surface to which the treatment is applied with rotation is smaller than 7.9, it is safe to say that the dispersion in hardness of the surface to which the treatment is applied with rotation is significantly smaller than the dispersion in hardness of the surface to which the treatment is applied at the rotation speed of 0 rpm with reliability of 97.5%. In the same manner, in carrying out the significant level 5% one-sided test, when the dispersion in hardness of the surface to which the treatment is applied with rotation is smaller than 9.3, it is safe to say that the dispersion in hardness of the surface to which the treatment is applied with rotation is significantly smaller than the dispersion in hardness of the surface to which the treatment is applied at the rotation speed of 0 rpm with reliability of 95%.

In this test, all dispersions in hardness of the surfaces to which the treatment is applied with rotation of the specimen are smaller than 9.3 and hence, the dispersion in hardness of the surface to which the treatment is applied with rotation is significantly smaller than the dispersion in hardness of the surface to which the treatment is applied at the rotation speed of 0 rpm with reliability of 95%. This implies that when the surface treatment is performed with the rotation of the specimen, the variation in the hardness of the formed film in the in-plane direction is decreased. Accordingly, it is evident that the formed film becomes homogeneous by performing the surface treatment while generating the controlled flow of the solution on the surface of the base material.

The dispersion in hardness of the surface to which the treatment is applied while rotating the specimen at 120 rpm or more is significantly smaller than the dispersion in hardness of the untreated surface to which only polishing is applied with reliability of 95%. This implies that it is possible to form a film which is more homogeneous than an air-formed film of the base material by controlling a flow speed of a treatment solution on a surface of the base material of the magnesium material.

Example 5

[Evaluation on Corrosion Based on Atmospheric Corrosion Test of Treated Film]

Using a pure magnesium extruded material (purity: 99.9%), an AZ31 extruded material and a magnesium alloy extruded material containing 0.3 wt % of Al (0.3% Al—Mg extruded material), a film containing calcium phosphate on a surface thereof is formed by the method explained in the example 1. Here, a specimen rotation speed is set to 0 rpm and 1440 rpm.

1 g/m$^2$ of NaCl is placed on a surface of a specimen. The specimen on which NaCl is placed is held in a temperature controlled bath in which relative humidity is held at 95% or more at a room temperature (25° C.). After 1 hour, 2 hours and 4 hours, an image of a total surface of each specimen is photographed by a CCD camera mounted on a stereoscopic microscope. A total area of a corroded portion is obtained from the image, and a corroded area ratio which is a ratio of a corroded area with respect to a total surface area is obtained. Changes with time of corroded area ratios of the pure magnesium extruded material, the AZ31 extruded material and the 0.3% Al—Mg extruded material are respectively shown in Table 4 and FIG. 21 to FIG. 23.

TABLE 4

Change with time of corroded area ratio of film

| Kind of base material | Rotation speed of specimen during treatment (rpm) | Corroded area ratio (%) | | |
|---|---|---|---|---|
| | | After 1 hour | After 2 hours | After 4 hours |
| Pure magnesium extruded material | untreated | 3.6 | 13.1 | 22.1 |
| | 0 | 2.5 | 3.8 | 5.5 |
| | 1440 | 0.3 | 1.7 | 8.2 |
| AZ31 extruded material | untreated | 4.1 | 6.6 | 9.8 |
| | 0 | 0.9 | 1.3 | 2.9 |
| | 1440 | 1.3 | 1.9 | 2.9 |
| 0.3% Al—Mg extruded material | untreated | 3.3 | 9.8 | 17.1 |
| | 0 | 0.8 | 1.5 | 3.6 |
| | 1440 | 0.5 | 0.8 | 1.4 |

Tendency that the corroded area ratio of the specimen treated at 1440 rpm is lower than the corroded area ratio of the specimen treated at 0 rpm is found with respect to all magnesium-based materials. From this result, it is evident that the corrosion resistance of the magnesium-based material against chloride ions is enhanced by forming the film under a flow with controlled speed of a solution on a surface of the specimen.

Magnesium-based materials are used not only as a biomaterial but also as a material of a part of a transport apparatus such as an automobile or a material of a casing of a house hold electric appliance or a communication apparatus. The corrosion of these materials is mainly caused by chloride ions. Since the corrosion due to NaCl placed on the surface can be suppressed by the surface treatment according to the method of the present invention, it is evident that the surface treatment method of the present invention is applicable to magnesium-based materials used in various applications.

Figure 21:
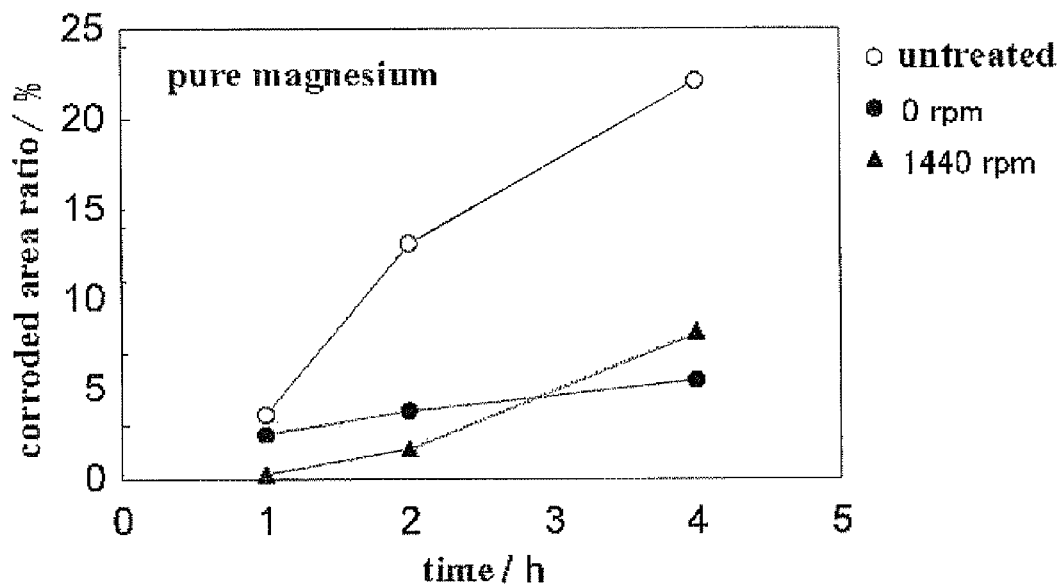
FIG. 21 A graph showing a change of a corroded area ratio (pure magnesium extruded material).
Figure 22:
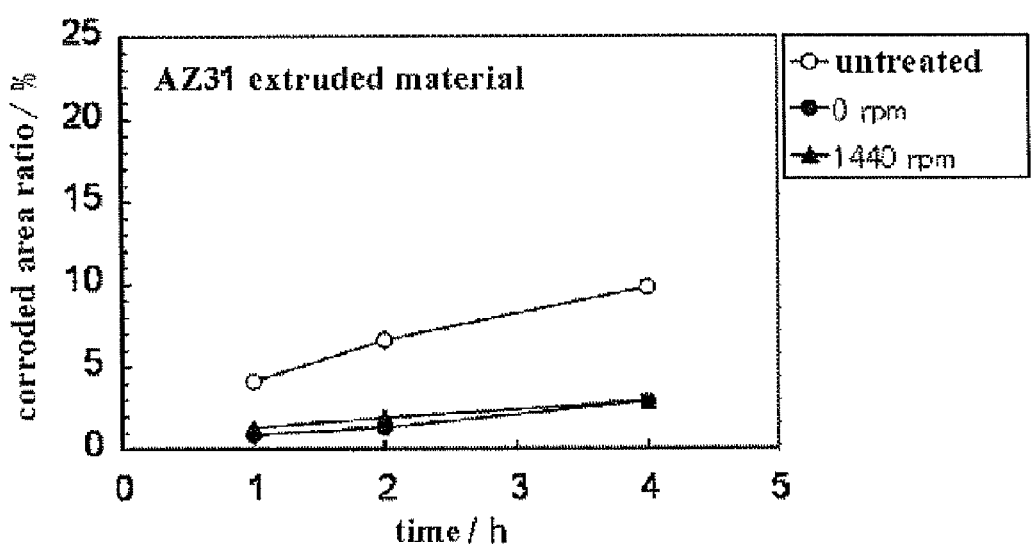
FIG. 22 A graph showing a change of a corroded area ratio (AZ31 extruded material).
Figure 23:
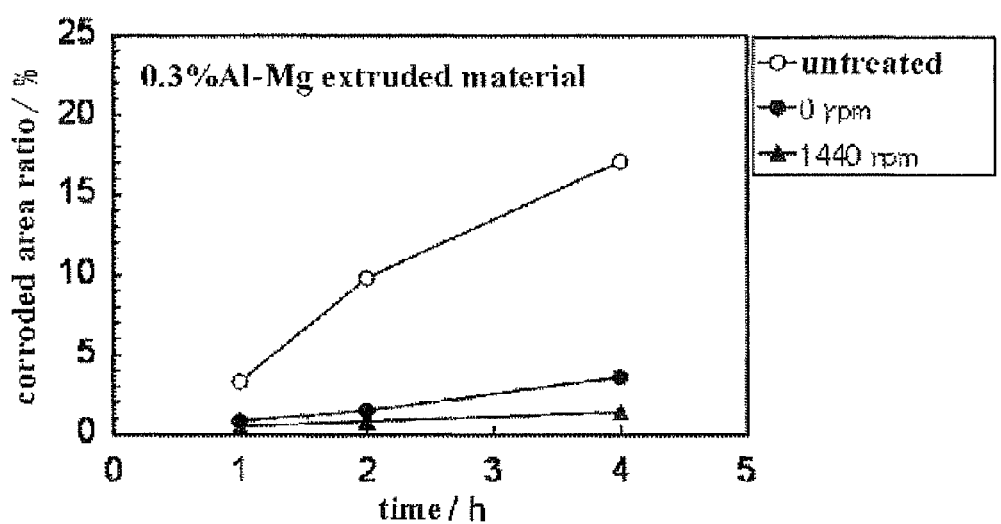
FIG. 23 A graph showing a change of a corroded area ratio (0.3% Al—Mg extruded material).

Further, from Table 4 and FIG. 21 to FIG. 23, it is found that in all magnesium-based materials, irrespective of the presence or the non-presence of rotation during the surface treatment, the corroded area ratio of the specimen treated with the calcium phosphate solution is lower than the corroded area ratio of the untreated specimen. From such a result, it is evident that the surface film containing calcium phosphate exhibits corrosion resistance against chloride ions.

Example 6

[Evaluation on Corrosion Resistance by Cyclic Dry and Wet Test of Treated Film of Screw-shaped Specimen]

A surface of a screw (AZ31, nominal size: M3×20 mm) made of a magnesium alloy is polished with a metal-use polishing agent, and a film containing calcium phosphate is formed on the surface of the screw in the same manner as the example 1. Here, a rotational axis of the screw specimen is set as a center axis of the screw in the longitudinal direction, and the screw is fixed to a jig with a screw head directed downwardly and a distal end of the screw directed upwardly. A rotation speed is set to 0 rpm and 1440 rpm.

1 g/cm$^2$ of NaCl is placed on a surface of the untreated specimen to which only polishing is applied and a surface of the specimen treated at 0 rpm or 1440 rpm, and these specimens are held in a temperature controlled box in which relative humidity is held at 95% or more. Then, a cyclic dry and wet test in which 1 cycle is constituted of 24 hours in total where temperature is switched to 25° C., 50° C. and 25° C. for every 8 hour is carried out 2 cycles repeatedly. After every 24 hours (completion of every 1 cycle), the screw specimen is lightly cleaned with ultra-pure water, and NaCl is placed on the screw specimen again. After 1 hour, 2 hours, 4 hours, 24 hours and 48 hours from starting of the test, a surface of each specimen is photographed by a CCD camera mounted on a stereoscopic microscope.

Figure 24:
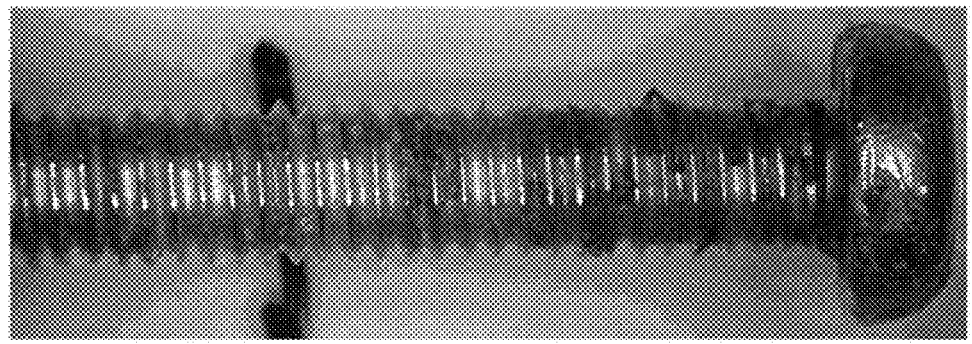
FIG. 24 A photograph showing a surface of a screw in an example 6 to which only polishing is applied.
Figure 25:
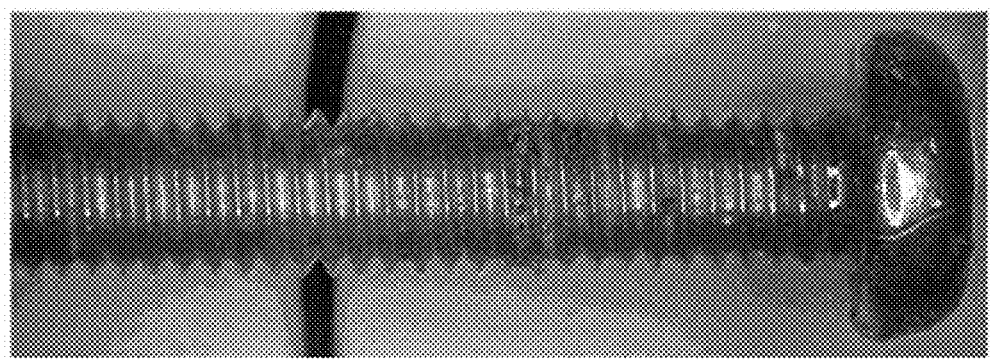
FIG. 25 A photograph showing a surface of a screw having a film which is treated at a rotation speed of 0 rpm in the example 6.
Figure 26:
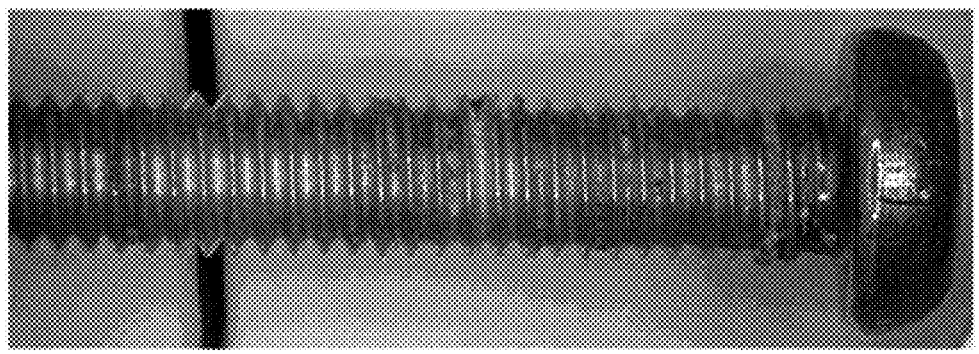
FIG. 26 A photograph showing a surface of a screw having a film treated at a rotation speed of 1440 rpm in the example 6.

FIG. 24 to FIG. 26 respectively show stereoscopic microscope images of surfaces of the respective screw specimens after 48 hours from starting of the test (after completion of 2 cycles). In all screw specimens, corrosion occurs along valleys of threaded grooves. Then, the number of threaded grooves in which the corrosion occurs is counted with respect to twenty threaded grooves formed on a portion of the screw specimen arranged in the direction toward a distal end of the screw specimen from the head of the screw specimen, and the number is summarized in Table 5.

TABLE 5

Frequency of occurrence of corrosion in cyclic dry and wet test of screw-shaped base

| Rotation speed of specimen during treatment (rpm) | Number of threaded grooves in which corrosion occurs per twenty threaded grooves (pieces) | | | | |
|---|---|---|---|---|---|
| | After 1 hour | After 2 hours | After 4 hours | After 24 hours | After 48 hours |
| untreated | 8 | 9 | 13 | 16 | 19 |
| 0 | 6 | 7 | 9 | 16 | 17 |
| 1440 | 4 | 5 | 10 | 13 | 14 |

In all times after starting the test, the number of threaded grooves in which the corrosion occurs in the screw specimen treated at 1440 rpm is smaller than the number of threaded grooves in which the corrosion occurs in the screw specimen treated at 0 rpm. From such a result, it is evident that the enhancement of the corrosion resistance of the magnesium-based material due to the film formation under a flow speed control of a treatment solution on a surface of the base material is effective irrespective of a shape of the base material.

With respect to the screw specimens after 48 hours from starting of the test (after completion of 2 cycles), to observe a corrosion state of a background magnesium material, a corroded product is removed using a chromic acid solution. With respect to twenty threaded grooves from which the number of threaded grooves on which the corrosion occurs is counted, an arbitrary portion having a length of 300 μm along the valley is measured by a laser microscope, and a maximum height (Ry: a total of a crest height and a valley height of concaves and convexes included in a standard length) which is a kind of line coarseness is obtained. In this test, it is considered that the larger the Ry, the deeper a corroded hole becomes.

Among Ry obtained with respect to twenty threaded grooves, measured values from the top to the fifth are shown in Table 6.

TABLE 6

Result of atmospheric corrosion test of screw-shaped base after 48 hours

| Rotation speed of specimen during treatment (rpm) | Top five measured values of Ry (μm) of corroded portions | | | | |
|---|---|---|---|---|---|
| Only polishing | 70.1 | 47.2 | 45.6 | 44.1 | 37.3 |
| 0 | 44.5 | 32.3 | 29.4 | 28.5 | 28.3 |
| 1440 | 44.5 | 28.1 | 26.2 | 22.9 | 20.9 |

Ry: maximum height of corroded portion which occurs in valley portions of threaded grooves.

Here observed is tendency that a depth of the corroded hole in the screw specimen treated at 1440 rpm is smaller than a depth of the corroded hole in the screw specimen treated at 0 rpm. From this result, it is evident that the formation of a film under a control of a flow speed of a solution has an effect of suppressing a progress of the corrosion of the magnesium material in the depth direction.

Further, irrespective of the presence or the non-presence of the rotation during the surface treatment, a depth of the corroded hole in the screw specimen treated with calcium phosphate solution is smaller than a depth of the corroded hole in the screw specimen to which only polishing is applied. From this result, it is evident that a film containing calcium phosphate is effective in the enhancement of the corrosion resistance of the magnesium material irrespective of a shape of a base material.

Example 7

[Evaluation on Corrosion Resistance of Magnesium-based Material Treated with Addition of Ultrasonic Oscillations by Immersion Test]

A pure magnesium extruded material (purity: 99.9%) and an AZ91 cast material are used. The specimen is fixed to a distal end of an ultrasonic oscillation generator using an instantaneous adhesive agent. While applying ultrasonic oscillations of frequency of 30 kHz and amplitude of 100 μm to the specimen, the specimen is immersed in a calcium phosphate solution which is the same as the solution used in the example 1 for 10 minutes thus forming a film containing calcium phosphate in a surface thereof. As a comparison material 1, in the method explained in the example 1, a film is formed on a surface of a pure magnesium extruded material and a surface of an AZ91 cast material while rotating the specimen at a rotation speed of 1440 rpm.

With respect to the specimens on which the surface film is formed by the above-mentioned respective methods, a portion of the surface of the specimen except for a predetermined area of the surface where the film is formed is covered with a silicone resin, and the specimen is immersed in a 3.5% NaCl-0.05M boric acid aqueous solution (pH: 9.3, NaCl boric acid buffering solution) aerated at room temperature for 1 hour. Thereafter, determination of magnesium ions dissolved in the NaCl boric acid buffering solution is performed by a xylidyl blue method, and a dissolved quantity of magnesium ions per unit area of the surface of the specimen is obtained. The dissolved quantity of magnesium ions is shown in Table 7.

TABLE 7

Change of dissolved quantity of magnesium ions due to difference in flow generating means

| Kind of base material | Method of generating flow on surface of base material | Dissolved quantity per unit area (mg/cm$^2$) |
|---|---|---|
| pure magnesium | Ultrasonic oscillations | 0.14 ± 0.07 |
|  | Rotation(1440 rpm) | 0.19 ± 0.06 |
| AZ31 extruded material | Ultrasonic oscillations | 0.67 ± 0.02 |
|  | Rotation(1440 rpm) | 0.71 ± 0.03 |

Each numerical value in Table indicates an average value ± standard deviation.

In both of the pure magnesium extruded material and the AZ91 cast material, the dissolved quantity of magnesium from the specimen having the film formed by applying ultrasonic oscillations is substantially equal to the dissolved quantity of magnesium from the specimen having the film formed with rotation at 1440 rpm. Accordingly, it is found from this example that, in addition to the means which applies the rotation to the base material, the means which applies ultrasonic oscillations to the base material is also effective as a means for generating a controlled flow between the surface treatment solution and the surface of the base material.

The invention claimed is:

1. A manufacturing method of a magnesium-based medical device,
wherein the magnesium-based medical device has a base material made of magnesium or a magnesium alloy and is dissolved and disappears in a living body,
wherein a corrosion-resistant film is formed on a surface of the base material,
wherein variation in a numerical value of hardness of the formed film expressed in terms of Vickers hardness is controlled corresponding to a desired corrosion resistance,
wherein the magnesium-based medical device has an in-plane direction, and
wherein a degree of variation in a numerical value of hardness of the formed corrosion-resistant film which is expressed in terms of Vickers hardness in the in-plane direction is adjusted by controlling the flow speed of the solution relative to the surface of the base material,
the method comprising:
immersing the base material in a solution in which components for forming the corrosion-resistant film are dissolved; and
in a state that the base material is immersed in a solution, depositing a corrosion-resistant film on the surface of the base material by generating a flow of the solution which has a flow speed relative to the surface of the base material, wherein homogeneity and corrosion resistance of the corrosion-resistant film are adjusted by controlling the flow speed of the solution relative to the surface of the base material, and wherein in vivo degradation speed of the corrosion-resistant film is controlled by adjusting the homogeneity and the corrosion resistance of the corrosion-resistant film.

2. The manufacturing method of claim 1, wherein the base material is immersed in a solution which contains phosphorous ions and calcium ions thus forming the corrosion-resistant film containing calcium phosphate on the surface of the base material.

3. The manufacturing method of claim 1, wherein the corrosion-resistant film contains calcium phosphate.

4. The manufacturing method of claim 3, wherein the base material is immersed in a solution which contains phosphorous ions and calcium ions thus forming the corrosion-resistant film containing calcium phosphate on the surface of the base material.

5. The manufacturing method of claim 3, wherein the solution comprises one or more elements selected from the group consisting of sodium biphosphate, dibasic sodium phosphate, sodium silicate, sodium aluminate, aluminum hydroxide, calcium chloride, and a calcium complex.

* * * * *